United States Patent [19]

Sweeny

[11] Patent Number: 4,528,226
[45] Date of Patent: Jul. 9, 1985

[54] STRETCHABLE MICROFRAGRANCE DELIVERY ARTICLE

[75] Inventor: Norman P. Sweeny, North Oaks, Minn.

[73] Assignee: Minnesota Mining and Manufacturing Co., St. Paul, Minn.

[21] Appl. No.: 540,500

[22] Filed: Oct. 11, 1983

[51] Int. Cl.³ .......................... A61L 9/04; B01J 13/00; D01F 1/02; D04H 1/04
[52] U.S. Cl. .................. 428/40; 252/522 A; 424/27; 427/171; 428/195; 428/201; 428/206; 428/289; 428/321.5; 428/354; 428/402.2; 428/402.21; 428/402.22; 428/402.24; 428/905
[58] Field of Search .............. 282/27.5; 428/321.1, 428/402.2, 402.21, 402.22, 905, 40, 195, 201, 206, 289, 343, 352, 354, 402.24; 252/522 R, 522 A; 346/214, 215; 424/27; 427/171

[56] References Cited

U.S. PATENT DOCUMENTS

| | | | |
|---|---|---|---|
| 3,516,846 | 6/1970 | Matson | 117/36.2 |
| 3,516,941 | 6/1970 | Matson | 252/316 |
| 3,578,545 | 5/1971 | Carson et al. | 428/905 |
| 3,755,064 | 8/1973 | Maierson | 428/905 |
| 3,778,383 | 12/1973 | Schibler | 252/316 |
| 4,087,376 | 5/1978 | Foris et al. | 252/316 |
| 4,089,802 | 5/1978 | Foris et al. | 252/316 |
| 4,100,103 | 7/1978 | Foris et al. | 252/316 |
| 4,251,386 | 2/1981 | Saeki et al. | 252/316 |
| 4,419,396 | 12/1983 | Sugimoto | 428/905 |

FOREIGN PATENT DOCUMENTS

| | | | |
|---|---|---|---|
| 1156725 | 7/1969 | United Kingdom | 428/402.21 |
| 2006709 | 5/1979 | United Kingdom | 428/402.21 |
| 2041319 | 9/1980 | United Kingdom | 428/402.21 |
| 2048206 | 12/1980 | United Kingdom | 428/402.21 |
| 2062570 | 5/1981 | United Kingdom | 428/402.21 |

Primary Examiner—Bruce H. Hess
Attorney, Agent, or Firm—Donald M. Sell; James A. Smith; Lorraine R. Sherman

[57] ABSTRACT

An article comprises sheet material which may be printed and having an adherent coating of microscopic, rupturable capsules in a binder on at least one surface thereof, the article being capable of undergoing plastic deformation and exhibiting:

(a) a yield point on a stress-strain curve of less than 225 kg/cm² (3200 psi) for a 127 micrometer (5 mil) thick material, (b) a difference in elongation at the yield point compared to the breaking point of at least 5.0 percent, and (c) an elongation at the yield point of less than 25 percent.

14 Claims, 1 Drawing Figure

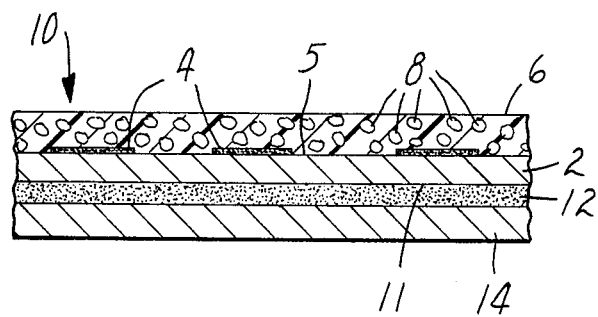

STRETCHABLE MICROFRAGRANCE DELIVERY ARTICLE

FIELD OF THE INVENTION

This invention relates to articles containing microscopic, discrete, rupturable capsules having releasable core material therein. In another aspect, it relates to a method for rupturing the microcapsules in the article and releasing the core material. The articles are useful for the release of fragrances, perfumes, and other materials.

BACKGROUND OF THE INVENTION

Microencapsulation is utilized to change the apparent state and properties of encapsulated core material, protect the material in a finely-divided form, control its release, and release the contents at the time desired.

In recent years, microcapsules have been used for image recording materials, medicines, perfumes, agricultural chemicals, adhesives, foods, detergents, dyes, solvents, catalysts, enzymes and rust inhibitors, specific examples being pressure-sensitive copying paper, aspirin capsules, perfume capsules, pressure-sensitive capsule adhesives, active charcoal capsules, enzyme capsules, liquid crystal capsules, and methylparathion capsules.

A wide variety of processes exist by which microcapsules can be manufactured. These varied processes provide different techniques for producing capsules of varying sizes, alternative materials for the composition of the capsule shell and various different functional materials within the shell. Some of these various processes are shown in U.S. Pat. Nos. 3,516,846; 3,516,941; 3,778,383; 4,087,376; 4,089,802; 4,100,103 and 4,251,386 and British Patent Specification Nos. 1,156,725; 2,041,319 and 2,048,206. A popular material for shell formation is the polymerization reaction product between urea and formaldehyde or melamine and formaldehyde, or the polycondensation products of monomeric or low molecular weight polymers of dimethylurea or methylated dimethylurea with aldehydes. A variety of capsule forming materials are disclosed, for example, in U.S. Pat. Nos. 3,516,846 and 4,087,376 and U.K. Patent Specification Nos. 2,006,709 and 2,062,570.

As shown in these references, the principal utility of microencapsulated materials is in the formation of a surface coated with the microcapsules in a binder. The microcapsules are ruptured by various means to release the material contained therein. In addition to release of physically observable materials such as ink in order to form a visible image, other types of active ingredients such as odor releasing materials, bacteriostatic materials, chemically active materials and the like have been provided in this manner.

Printed articles capable of undergoing either plastic or inelastic deformation, but without an applied layer of microscopic rupturable capsules, are known in the art, such as printed "silly putty".

Web, film and sheet materials coated with a microcapsule containing layer, where the release of the liquid phase, vaporizable solid, or solid dispersed in a liquid is stimulated by pressure or by shear applied to the microcapsule layer, e.g., by scratching or scraping with a fingernail, are also known in the art. These are available, for example, as scratch 'n' sniff stickers.

SUMMARY OF THE INVENTION

The present invention provides an article containing microscopic rupturable capsules, which capsules upon rupture release core material, said article comprising:
(1) a support layer comprising printed sheet material capable of undergoing plastic or inelastic plastic deformation, and
(2) a coating layer comprising microscopic, rupturable capsules with releasable core material therein in a binder coated on at least one surface thereof;
said article exhibiting
(a) a yield point on a stress-strain curve of less than 225 kg/cm$^2$ (3200 psi) for a 127 micrometer (5 mil) thick material, and preferably in the range of 20–200 kg/cm$^2$,
(b) a difference in elongation at the yield point compared to the breaking point of at least 5.0 percent and preferably in the range of 10 to 200 percent, and
(c) an elongation at the yield point of less than 25 percent, preferably in the range of 0.1 to 10 percent.

Optionally, the second surface of the sheet material may have adhered thereto an adhesive layer which preferably is pressure sensitive. Optionally, the adhesive layer may have a release liner attached.

In another aspect, the present invention provides a method for releasing core material from the article of the invention by application of tensile stress, e.g., by being stretched by hand, the tensile stress being sufficient to cause plastic deformation of the article which results in distortion of the printed image which may be present and also rupture of at least some of the microscopic capsules in the coated layer. Such rupture of capsules releases core material.

In the present application:

"plastic or inelastic deformation" means permanent alteration of the form of a plastic substance under stress i.e., substance can no longer return to its original unspoiled form;

"elongation" means an increase in length of a material before it is fractured when subjected to stress, usually expressed as a percent of its original length;

"tensile strength" or "tensile rupture strength" means the breaking strength of a substance, which may be a composite article, when subjected to a tensile (stretching) force;

"cohesive tensile strength" or "cohesive strength" means the tensile strength of a specified material;

"yield point" means the point on any stress-strain diagram at which there is a marked increase in strain without a material increase in stress (i.e., the substance will no longer show total elastic recovery);

"volume payload" of capsules means the ratio of the volume of core material to total capsule volume $\times$ 100; and "flexible" means can be bent at an angle of 120° without fracturing.

BRIEF DESCRIPTION OF THE DRAWING

The drawing shows an enlarged cross-sectional view of an article of the invention.

DETAILED DESCRIPTION OF THE INVENTION

The present invention provides an article comprising a sheet material which may be printed and having an adherent coating of microscopic rupturable capsules in a binder on at least one surface thereof, the article being capable of undergoing plastic deformation and exhibiting:

(a) a yield point on a stress-strain curve of less than 225 kg/cm² (3200 psi) for a 127 micrometer (5 mil) thick material,
(b) a difference in elongation at the yield point compared to the breaking point of at least 5.0 percent, and
(c) an elongation at the yield point of less than 25 percent, preferably in the range of 0.1 to 10 percent.

As shown in the drawing, in one embodiment the article of the invention 10 comprises sheet material 2, which is capable of undergoing plastic deformation, having printed image 4 thereon. A layer 6 containing microscopic rupturable capsules 8 with releasable core material therein in a binder is adhered to printed surface 5 of sheet material 2. Preferably, article 10 may have coated on second surface 11 of sheet material 2 adhesive layer 12 and optionally thereon release liner 14. When adhesive layer 12 is present, article 10 can be releasably attached to a flexible support with a release surface thereon such as paper, fabric, polyester film, polyethylene terephthalate film, or the like, or a rigid support such as metal, glass, ceramic, or the like.

The support, which preferably is a sheet material, may be a film, web, or sheet material of woven or nonwoven construction, and may effectively be of any composition capable of plastic deformation such as polymeric film or fabric, but generally flexible sheets of organic polymeric film are preferred.

The support may optionally be treated on the top surface as by priming, abrasion or corona discharge, by methods known in the art, to aid the development of adhesion between the film, web, sheet material, or other support and the microcapsule-containing layer. The support may be of any desired thickness, preferably in the range of 50 to 1500 micrometers and most preferably 50 to 300 micrometers thick.

The support, particularly when it is a flexible sheet material, may be optionally coated on the back side with an adhesive, preferably pressure-sensitive or a solvent (e.g., water)-moistenable adhesive, such as a polyurethane, polyacrylate, polyvinyl resin, polyamide, polyester, polyolefin, silicone, or containing starch, gum arabic, gelatin, and the like. An optional release liner may also be present. This is desirable if the adhesive is a pressure-sensitive adhesive. Release liners are known in the art and are disclosed, for example, in U.S. Pat. No. 4,386,135.

The capsules in the present invention may comprise any rupturable capsule containing an active ingredient therein. Material contained within the capsule walls, i.e., the capsular internal phase or capsule core material, is relatively unimportant to the practice of the invention and can be any material which is substantially water-insoluble and which does not interact with the intended capsule wall material, or with other encapsulating-system components, to the detriment of the process. A few of the materials which can be utilized as capsule internal phases include, along a multitude of others: water-insoluble or substantially water-insoluble liquids, such as odor-releasing materials, olive oil, fish oils, vegetable oils, sperm oil, mineral oil, xylene, toluene, kerosene, chlorinated biphenyl, and methyl salicylate; similar substantially water-insoluble materials of a solid but meltable nature such as naphthalene and cocoa butter; fragrances; reactants; biocidal compositions; physiological compositions; and the like. The tensile rupture strength of the capsules should be less than the cohesive tensile strength of the binder used. It has also been found that the size of the capsules plays an important role in the usefulness of capsules within rupturable sheets according to the practice of the present invention. Generally the capsules should have a volume payload between 50 and 90%, preferably between 60 and 85%, and a 50% average volumetric size between 5–35 micrometers, preferably 12 to 25 micrometers. The dried layer containing the microcapsules should contain between 30 and 70% microcapsules (by weight), preferably between 50–65%. These dimensions play a useful role in the ability to control the percentage of rupture of capsules in the practice of the present invention. With lower payloads (e.g., 60 to 65%), the capsules should be larger to provide the necessary tensile rupture strength. The broadest range of capsule size under any conditions would be about 6 to 35 micrometers, preferably with 10 to 25 micrometer capsules used with a 70 to 90% by weight payload.

As previously noted, the size of the capsules has an effect upon the practice of the present invention. With capsules less than 10 micrometers in diameter, there is less rupturing of the capsules with a given shear so as to reduce the useful release of materials. Above 30 micrometers, the particles are so large that they may readily burst by handling of the sheets and manufacturing procedures unless thicker shells are provided, which reduce the payload. The preferred range of 12 to 25 micrometers is therefore important to the practice of the present invention.

The binder material of the coating layer must form a bond to the support which is stronger than the cohesive strength of the binder with the capsules dispersed therein. Although it is generally desirable to have a binder, the cohesive strength of which is less than its adhesive strength to the support, this is not essential. When capsules are included within the binder composition, the effective cohesive strength of the binder tends to be reduced. Binder compositions, which by themselves would cause a support to be damaged when subjected to stress, can be used in combination with capsules in the practice of the present invention because of lowered effective cohesive strength. Binders useful in the present invention include polyvinyl resins (e.g., polyvinyl alcohol, polyvinyl chloride), polyurethanes, polyesters, polyamides and organic film-forming polymeric binders in general.

In effect, to best practice the present invention it is desirable that certain properties within the article have relative values for each of the materials used. The cohesive strength of the support should exceed the adhesive strength between the coating layer and the support. The adhesive strength of the coating layer to the support should exceed the cohesive strength of the coating layer (i.e., binder and capsules therein). The cohesive strength of the binder should exceed the tensile rupture limits of the capsules.

In the practice of the invention, the article, if strippably attached to a support, is removed therefrom. As noted above, the article may be releasably attached to a support which preferably is flexible. The article is then subjected to tensile stress, for example, as by stretching with the hands, sufficient to cause plastic deformation of the article and thereby cause controllable distortion of the printed image and rupture of at least some of the microscopic capsules in the coated layer. Rupture of capsules results in release of liquid, solid dispersed in a liquid, or vaporizable liquid encapsulated therein. The odor of readily vaporizable substances is immediately noticeable. Some encapsulated substances, upon release, may be rubbed on the skin to facilitate their use. Additional application of tensile stress to the article generally results in additional distortion of the printed image and additional release of encapsulated substance, thereby enabling the article to be used many times. Easily deformable articles tend to release more encapsulated substance upon application of tensile stress than those having a higher yield point on a stress-strain curve. In the alternative, core material may be released by application of pressure or shear forces (as by scratching with a fingernail) to the article. If the article has an optional pressure-sensitive layer on the second surface of the support layer, it may be adhesively attached to a second surface.

The articles of the present invention are useful as toys and for the delivery of fragrances, perfumes, and other liquid and solid substances.

Objects and advantages of this invention are further illustrated by the following examples, but the particular materials and amounts thereof recited in these examples, as well as other conditions and details, should not be construed to unduly limit this invention.

EXAMPLE

A solution of 18.6 percent by weight microencapsulated grape fragrance, prepared according to U.S. Pat. No. 3,516,941, and 13.3 percent by weight of polyvinyl alcohol (Gelvatol 40-10 ™, Monsanto) was applied to printed 102 micrometers thick (4 mil) white Type G Vinyl TC (Fasfilm Prod. Co.), a flexible vinyl film material, by a rotogravure process using a 55 line quadrangular roll with a cell depth of 108 micrometers. The applied layer was oven dried. The printed region was die cut from the unprinted film material to give a printed "label." This "label" when stretched by hand gave a controllable distortion of the printed image and some release of the microencapsulated fragrance. The article exhibited a yield point of 121 kg/cm$^2$, a difference in elongation at the yield point compared to the breaking point of 5.2 percent, and elongation at the yield point of 3.1 percent.

Various modifications and alterations of this invention will become apparent to those skilled in the art without departing from the scope and spirit of this invention, and it should be understood that this invention is not to be unduly limited to the illustrative embodiments set forth herein.

I claim:

1. An article containing microscopic rupturable capsules, which capsules upon rupture release core material, said article comprising:
    (1) a support layer comprising printed sheet material of polymeric film or fabric capable of undergoing plastic deformation, and
    (2) a coating layer comprising microscopic, rupturable capsules with releasable core material therein in a binder coated on at least one surface thereof;
    said article exhibiting
    (a) a yield point on a stress-strain curve of less than 225 kg/cm$^2$ for a 127 micrometer thick material,
    (b) a difference in elongation at the yield point compared to the breaking point of at least 5.0 percent, and
    (c) an elongation value at the yield point of less than 25 percent.

2. The article according to claim 1 wherein said yield point is in the range of 25 to 200 kg/cm$^2$.

3. The article according to claim 1 wherein said support is a flexible sheet material.

4. The article according to claim 3 wherein said sheet material is a polymeric film.

5. The article according to claim 1 wherein said capsules have an average diameter in the range of 5 to 35 micrometers.

6. The article according to claim 1 wherein said capsules have an average size in the range of 12 to 25 micrometers.

7. The article according to claim 1 wherein the difference in elongation at the yield point compared to the breaking point is in the range of 10 to 200 percent.

8. The article according to claim 1 wherein the elongation at the yield point is in the range of 0.1 to 10 percent.

9. The article according to claim 1 wherein said capsules comprise in the range of 30 to 70 percent of the weight of said coating layer.

10. The article according to claim 1 wherein the volume payload of said capsules is in the range of 60 to 85 percent.

11. The article according to claim 1 wherein said core material is an odor-releasing substance.

12. The article according to claim 1 further comprising an adhesive layer coated on the second surface or said support.

13. The article according to claim 12 further comprising a release liner overlying said adhesive layer.

14. A method for rupturing microcapsules contained in an article comprising the steps of:
    (a) providing an article containing microscopic rupturable capsules, which capsules upon rupture release core material, said article comprising:
        (1) a support layer comprising printed sheet material capable of undergoing plastic deformation, and
        (2) a coating layer comprising microscopic, rupturable capsules with releasable core material therein in a binder coated on at least one surface thereof;
        said article exhibiting
        a. a yield point on a stress-strain curve of less than 225 kg/cm$^2$ for a 127 micrometer thick material,
        b. a difference in elongation at the yield point compared to the breaking point of at least 5.0 percent, and
        c. an elongation at the yield point of less than 25 percent;
    (b) applying tensile stress to said article sufficient to cause rupture of at least same of said capsules, so as to release core material therefrom.

* * * * *